United States Patent [19] [11] 4,195,363
Jenson [45] Apr. 1, 1980

[54] PERIMETER DRAFT WELDING HOOD

[76] Inventor: Bernard T. Jenson, 34762 Powder River Pl., Fremont, Calif. 94536

[21] Appl. No.: 865,994

[22] Filed: Dec. 30, 1977

[51] Int. Cl.² .............................................. A61F 9/06
[52] U.S. Cl. ........................................ 2/8; 2/DIG. 1
[58] Field of Search ...................... 2/8, 171.3, 9, 10, 5, 2/DIG. 1; 128/142.3, 142.7

[56] References Cited

U.S. PATENT DOCUMENTS

| 3,657,740 | 4/1972 | Cialone | 2/8 |
| 3,921,223 | 11/1975 | Hoyecki | 2/8 |
| 3,922,722 | 12/1975 | Pokhodnya et al. | 2/8 |

FOREIGN PATENT DOCUMENTS 2409198 9/1975 Fed. Rep. of Germany ................ 2/8

Primary Examiner—Peter Nerbun

[57] ABSTRACT

A mask or hood worn by a welding or grinder operator includes a manifold extending along the lower perimeter thereof below the chin of the operator. The manifold is provided with a plurality of holes or slots which vent pressurized air downwardly. The downwardly vented air forms an air curtain which prevents entry under the hood of smoke and noxious fumes created by the welding or grinding process. The manifold is supplied by a flexible tube which is connected between one end of the manifold and an air blower which may be secured to the operator's body, preferably at the waist, or which may be located remotely. The body-carried air blower is provided with a rechargeable battery pack.

9 Claims, 5 Drawing Figures

U.S. Patent  Apr. 1, 1980  4,195,363
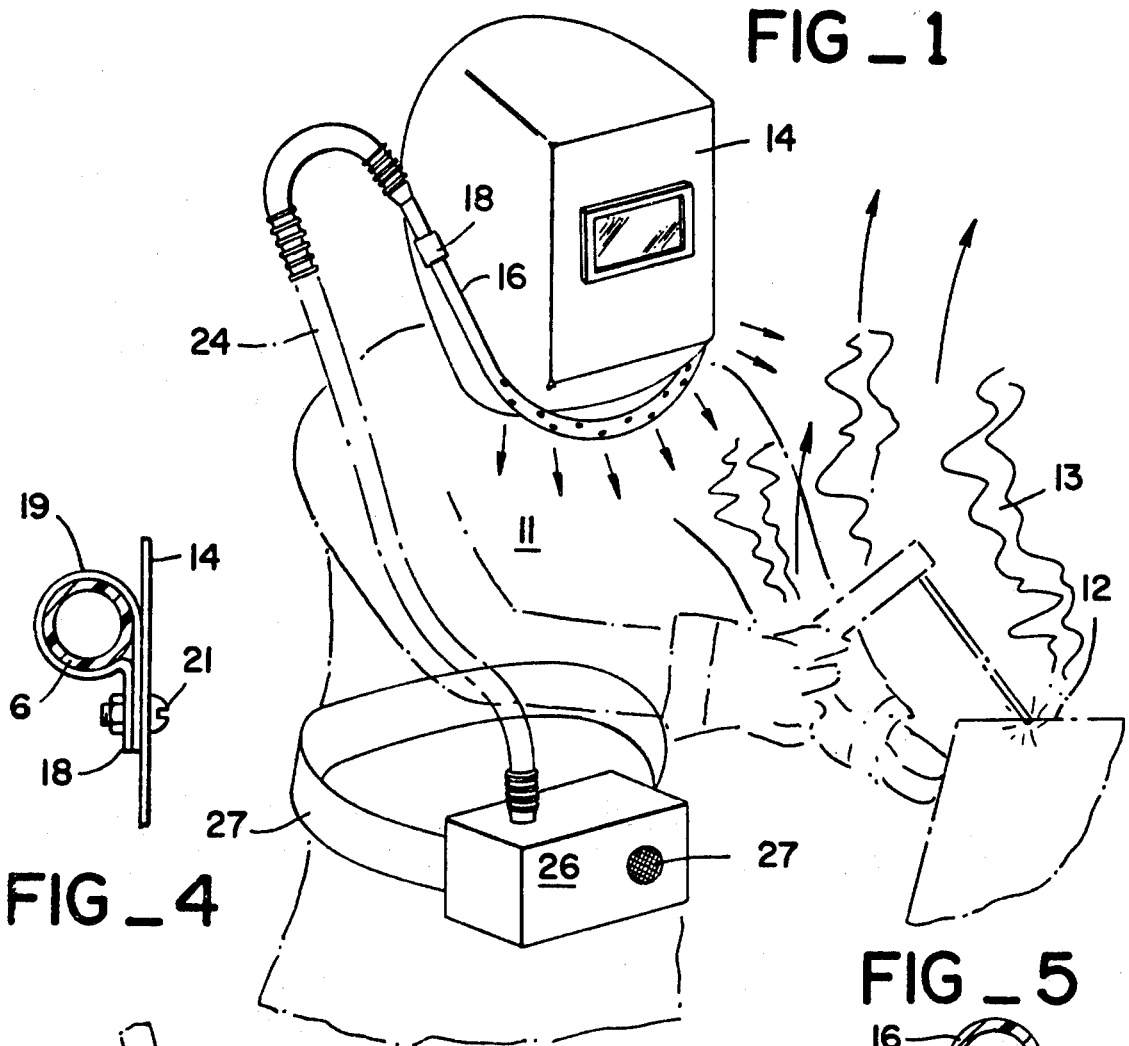
FIG_1
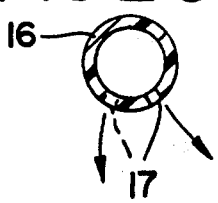
FIG_5
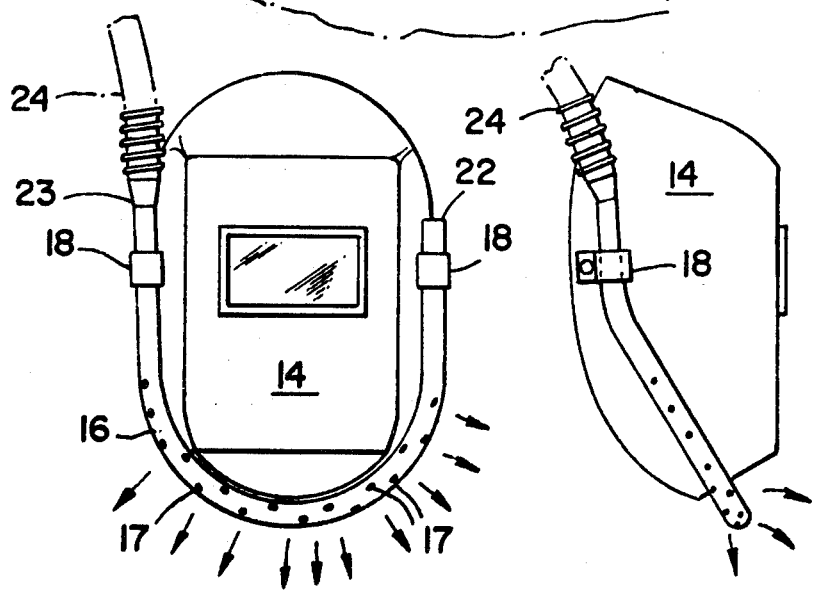
FIG_4
FIG_2
FIG_3

PERIMETER DRAFT WELDING HOOD

BACKGROUND OF THE INVENTION

It is well recognized that many industrial processes, such as welding, grinding, and the like, produce voluminous quantities of smoke, soot, fine particles, both at high and ambient temperatures, and noxious fumes. Workers in these fields are often provided with protection from flying particles and intense light, such as the welding hood which is commonly worn by the worker over the face and head. Often, there is little or no protection from the smoke and fumes.

It has been found that inhalation of the smoke and fumes is detrimental to the health of the workers in these fields. Furthermore, the smoke and noxious fumes greatly decrease the productivity of the worker, and also obscure the view of the work in progress. Thus, it also affects the quality of the finished product.

The prior art is replete with attempts to remove the unhealthy and unproductive effects of the smoke and noxious fumes. The following patents are the most pertinent:

U.S. Pat. No. 2,688,962
U.S. Pat. No. 3,098,233
U.S. Pat. No. 3,181,532
U.S. Pat. No. 3,353,191
U.S. Pat. No. 2,444,393
U.S. Pat. No. 3,467,965
U.S. Pat. No. 3,584,314
U.S. Pat. No. 3,657,740
U.S. Pat. No. 3,881,478

One form of device known in the prior art for attenuating smoke and fumes from welding and grinding involves the use of ducts which are provided with openings directly adjacent to the work site. The ducts lead to ceiling mounted air cleaning devices which include suction fans and multi-stage filters. Although these devices work well, it is often difficult to justify the great expense involved in installation and maintenance of these air cleaning devices.

Also known in the prior art are air systems which provide a curtain of air flowing between the inner surface of the welding hood and the face of the welding operator. Some of these devices require fresh outside air to form the air curtain, and thus necessitate the installation of extensive duct work. Others of these devices use recirculated air which is provided by a blower system and a multi-stage filter. It may be appreciated that recirculated air must be highly filtered to remove the dust and smoke particles which are found in the work area. Also, temperature conditioning of the air is often required. Thus these systems are also rather expensive, and the filtering system requires continual maintenance and meticulous monitoring.

Both types of prior art system are extremely limiting in that the welding or grinding work to be done must be brought within the operational proximity of the air supply devices. In many kinds of industrial manufacturing and fabrication, especially on large structures or devices, the work site cannot be brought into proximity with the air supply device. In these situations, the worker must suffer the effects of the smoke and noxious fumes.

SUMMARY OF THE PRESENT INVENTION

The present invention generally comprises a device for protecting a worker from the noxious fumes and smoke generated by welding, grinding, and similar endeavors. It operates on a principle not found in similar prior art devices; that is, it creates a curtain of air extending from the lower edge portion of the hood or mask, the air curtain preventing migration of smoke or fumes under the hood. Thus, the smoke and noxious fumes are blown away from the mask, and the worker is able to breathe ambient air.

The invention includes a manifold which extends along the lower edge portion of the hood or mask, in the general area of the chin and mandible portion of the hood. The manifold is provided with a plurality of holes or slots which vent pressurized air in a general downward direction. The vented air provides the air curtain which blows the smoke and fumes away from the head of the worker.

The manifold is supplied by a flexible hose which is connected to an air blower. Due to the fact that the air supplied by the present invention is not breathed by the worker, the filter requirements for the air ejected by the manifold are non-existent. Thus, a salient feature of the present invention is that the air blower can be a portable device strapped to the body of the worker, preferably about the waist. This blower unit is powered by a rechargeable battery pack. Thus, the worker is not restrained by any ducting or power supply lines, and may move to any location to accomplish the requires task. In another form, a centrally located air supply, such as a blower, can serve one or more stationary workers through a duct or hose supply system.

A BRIEF DESCRIPTION OF THE DRAWINGS

FIG. 1 is a perspective view showing the present invention in a typical working situation.

FIG. 2 is a front view of the manifold portion of the present invention.

FIG. 3 is a side view of the manifold portion of the present invention.

FIG. 4 is a cross-sectional view showing the mounting means for securing the present invention to a welding hood.

FIG. 5 is a cross-sectional view of the manifold portion of the present invention.

DESCRIPTION OF THE PREFERRED EMBODIMENT

The present invention generally comprises a device, used by a worker employed in a task which creates noxious fumes and smoke, for directing those fumes and smoke away from the face of the worker. As shown in FIG. 1 of the accompanying drawings, the worker 11 may be doing some task, such as welding, at a work location 12. The smoke, fumes, or dust 13 which arise from the work site 12 generally flow directly past the face of the worker. Generally speaking, the worker 11 is provided with a mask or hood, such as the welding hood 14. Commonly, some of the smoke and fumes 13 arising from the work site 12 will flow underneath the lower edge of the mask, and be inhaled by the worker. The smoke and fumes also affect the vision of the worker. Of course, these effects are detrimental to the health of the worker.

The present invention includes a manifold 16 formed in a general U-shape and secured to the lower edge of the hood 14 by means of brackets 18. The manifold 16 is provided with a plurality of holes or vents 17 disposed in the outer circumferential portion of the U-shape thereof. As shown in FIGS. 1–3, and 5, the vents 17 discharge pressurized air to form an air curtain extending downwardly from the lower edge of the hood 14. This air curtain prevents the smoke and fumes 13 from migrating under the hood 14, so that the worker 11 may breathe fresh air which enters beneath the hood 14 through the gap at the top and rear thereof, by natural processes.

Each of the clamps 18 is disposed at a distal end of the U-shaped manifold 16, as shown in FIG. 2, and at intermediate locations (not shown). With reference to FIG. 4, each of the clamps 18 includes a generally circular loop portion 19 which encircles the generally cylindrical manifold 16. The clamp 18 is secured to the hood 14 by means of a screw and nut assembly 21. Such clamps are well known in the art, as is the welding hood 14.

One end 22 of the manifold 16 is blocked, while the other end 23 is joined to a flexible air hose 24. The air hose 24 extends to a blower unit 26, which is either secured to the body of the worker 11 or located remotely. In the preferred embodiment, the blower unit 26 is secured to the waist of the worker 11 by means of a belt 27 extending thereabout.

It should be noted that due to the flexibility of the air hose 24, the hose will not be crimped by the worker 11 raising the hood 14. Thus the air flow from the manifold 16 will continue when the hood is raised. Also, the connection of the hose 24 to the blower unit 26 may comprise any one of several forms of slip-on or snap-on hose connections known in the prior art. Also, in the preferred embodiment, the blower unit 26 incorporates a rechargeable battery pack to power the electric motor which in turn drives the blower. Thus, the present invention is completely portable, and may be carried to the vicinity of any work location 12, as desired by the worker.

It should be noted that the air provided by the blower unit 26 through the air hose 24 into the manifold 16 issues from the manifold in an air curtain which is downwardly directed away from the mask 14. Thus, the air provided by the present invention is not breathed by the worker 11. There is no need to filter the incoming air since the worker does not breathe the air from the present invention.

It should be noted that although the preferred embodiment is described with reference to welding and its use with a welding hood, the invention is not limited to this use. It may be used effectively in conjunction with any endeavor in which noxious fumes, smoke, or dust are created, and in which the worker wears a protective mask to which the invention may be attached.

I claim:

1. A device for preventing the migration of smoke and noxious fumes beneath a protective face shield worn by a worker, said device comprising a tube-like manifold secured to the exterior of said face shield adjacent the lower edge of said face shield, said manifold including a plurality of spaced vent holes positioned in said manifold so as to direct a curtain of air downwardly from said manifold to prevent migration of the smoke and fumes and said curtain of air under the lower edge of said face shield, said device further including means for supplying a flow of pressurized air to said manifold to produce said downwardly directed air curtain.

2. The device of claim 1, wherein said manifold extends adjacent to the lower edge and side portions of said face shield.

3. The device of claim 1, wherein said manifold comprises a generally U-shaped tube.

4. The device of claim 1, wherein said vent holes are directed downwardly and outwardly along the lower edge of said face shield.

5. The device of claim 1, wherein said blower unit is secured to the body of said worker in a portable fashion.

6. The device of claim 5, wherein said blower unit is self-powered by a rechargeable energy source.

7. The device of claim 1, further including a pair of clamps secured to the temple portion of said face shield, said clamps engaging the end portions of said U-shaped manifold.

8. The device of claim 1 wherein said airflow means comprises a blower unit.

9. The device of claim 1 wherein said U-shaped manifold includes a closed end and a supply end, said device further including a flexible air hose extending between said airflow means and said supply end of said manifold.

* * * * *